(12) United States Patent
Dell'Oca

(10) Patent No.: US 9,642,660 B2
(45) Date of Patent: May 9, 2017

(54) MINIMALLY INVASIVE CRIMP AND CABLE FOR BONE CERCLAGE

(75) Inventor: Alberto A. Fernandez Dell'Oca, Montevideo (UY)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1018 days.

(21) Appl. No.: 13/310,244

(22) Filed: Dec. 2, 2011

(65) Prior Publication Data

US 2013/0018375 A1 Jan. 17, 2013

Related U.S. Application Data

(60) Provisional application No. 61/508,633, filed on Jul. 16, 2011.

(51) Int. Cl.
*A61B 17/82* (2006.01)
*A61B 17/88* (2006.01)

(52) U.S. Cl.
CPC .......... *A61B 17/82* (2013.01); *A61B 17/8869* (2013.01)

(58) Field of Classification Search
USPC ........................... 606/74, 103, 323–324, 328
See application file for complete search history.

(56) References Cited

U.S. PATENT DOCUMENTS

| | | |
|---|---|---|
| 5,536,270 A | 7/1996 | Songer et al. |
| 5,649,927 A | 7/1997 | Kilpela et al. |
| 5,908,421 A | 6/1999 | Beger |
| 6,077,268 A | 6/2000 | Farris et al. |
| 6,387,099 B1 | 5/2002 | Lange et al. |
| 7,207,993 B1 | 4/2007 | Baldwin et al. |
| 7,250,054 B2 | 7/2007 | Allen et al. |
| 2004/0199169 A1 | 10/2004 | Koons et al. |
| 2005/0149086 A1 | 7/2005 | Huxel et al. |
| 2007/0043377 A1 | 2/2007 | Fernandez |
| 2010/0274249 A1 | 10/2010 | Dell'Oca |

FOREIGN PATENT DOCUMENTS

| | | | |
|---|---|---|---|
| EP | 0 625 336 | 11/1994 | |
| WO | 95/22294 | 8/1995 | |
| WO | 2010/011718 | 1/2010 | |
| WO | WO 2010011718 A1 * | 1/2010 | ............. A61B 17/58 |
| WO | 2010/014119 | 2/2010 | |
| WO | 2010/124211 | 10/2010 | |

* cited by examiner

*Primary Examiner* — Andrew Yang
(74) *Attorney, Agent, or Firm* — Fay Kaplun & Marcin, LLP

(57) ABSTRACT

A crimp configured to fix a cable about a bone includes a body extending from a proximal end to a distal end and a first channel extending through the body from the proximal end to the distal end, the first channel being sized and shaped to permit a cable to be slid therethrough along with a second channel extending through the body from the proximal end to the distal end, the second channel being sized and shaped to permit a cable to be slid therethrough and a deformable extension attached to the proximal end of the body, the extension including a lumen aligned with the second channel and sized and shaped to permit the cable to be slid therethrough.

15 Claims, 17 Drawing Sheets

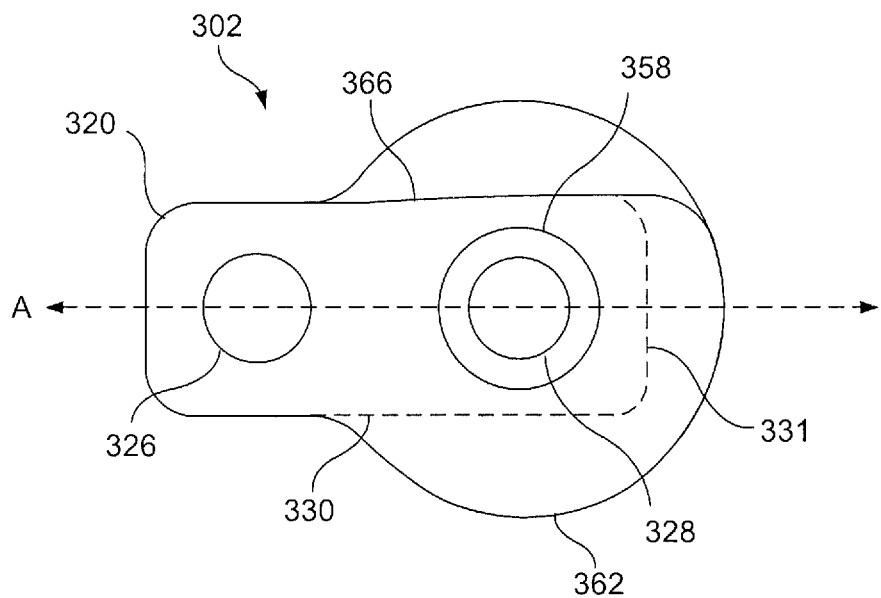
F I G. 18
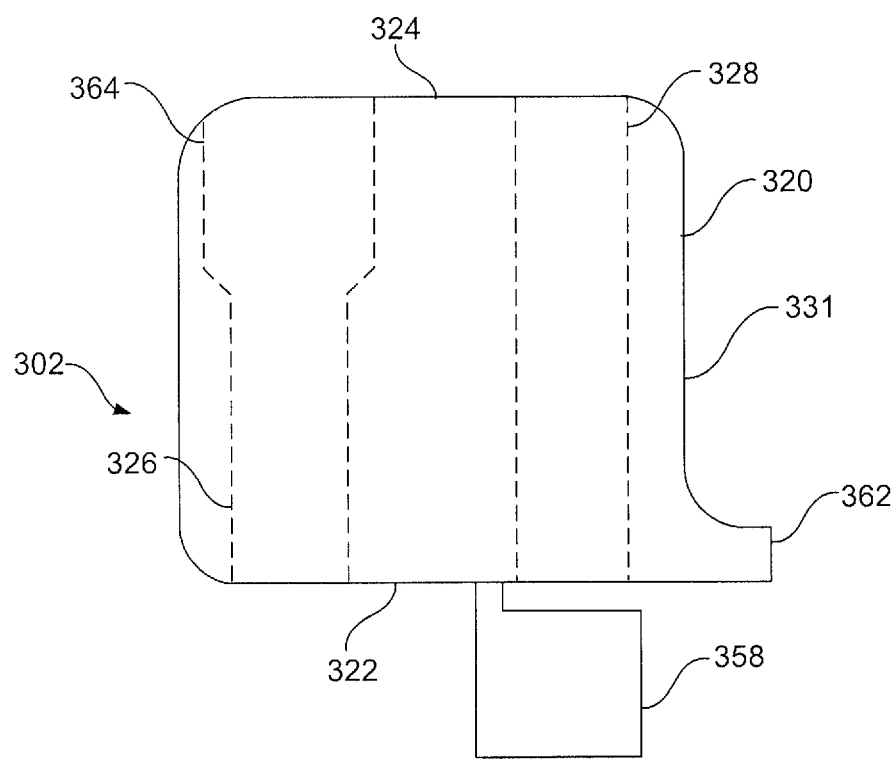
F I G. 19

MINIMALLY INVASIVE CRIMP AND CABLE FOR BONE CERCLAGE

PRIORITY CLAIM

The present application claims priority to U.S. Provisional Application Ser. No. 61/508,633 filed on Jul. 16, 2011 and entitled "Minimally Invasive Flippable Crimp and Cable for Bone Cerclage," the entire disclosure of which is incorporated herein by reference.

FIELD OF THE INVENTION

The present invention relates to surgical methods and devices for the repair of bone and, in particular, to methods and devices for bone fixation using a cable cerclage technique.

BACKGROUND

Portions of a fractured or otherwise surgically separated bone may be fixed relative to one another via a tensioned cable encircling the bone and a crimp deformed thereover to fix the cable over the bone. Although instruments for minimally invasive looping of the cable around the bone are available, a large incision is still required for the crimping process as most crimping tools insertable through a small incision are not strong enough to deform a crimp at the required depth within the wound.

SUMMARY OF THE INVENTION

The present invention is directed to a crimp configured to fix a cable about a bone, comprising a body extending from a proximal end to a distal end and a first channel extending through the body from the proximal end to the distal end, the first channel being sized and shaped to permit a cable to be slid therethrough along with a second channel extending through the body from the proximal end to the distal end, the second channel being sized and shaped to permit a cable to be slid therethrough and a deformable extension attached to the proximal end of the body, the extension including a lumen aligned with the second channel and sized and shaped to permit the cable to be slid therethrough.

BRIEF DESCRIPTION OF THE DRAWINGS

FIG. 18 shows another side view of a crimp of the system of FIG. 17; and

FIG. 19 shows a top plan view of the crimp of the system of FIG. 17.

DETAILED DESCRIPTION

Figure 1:
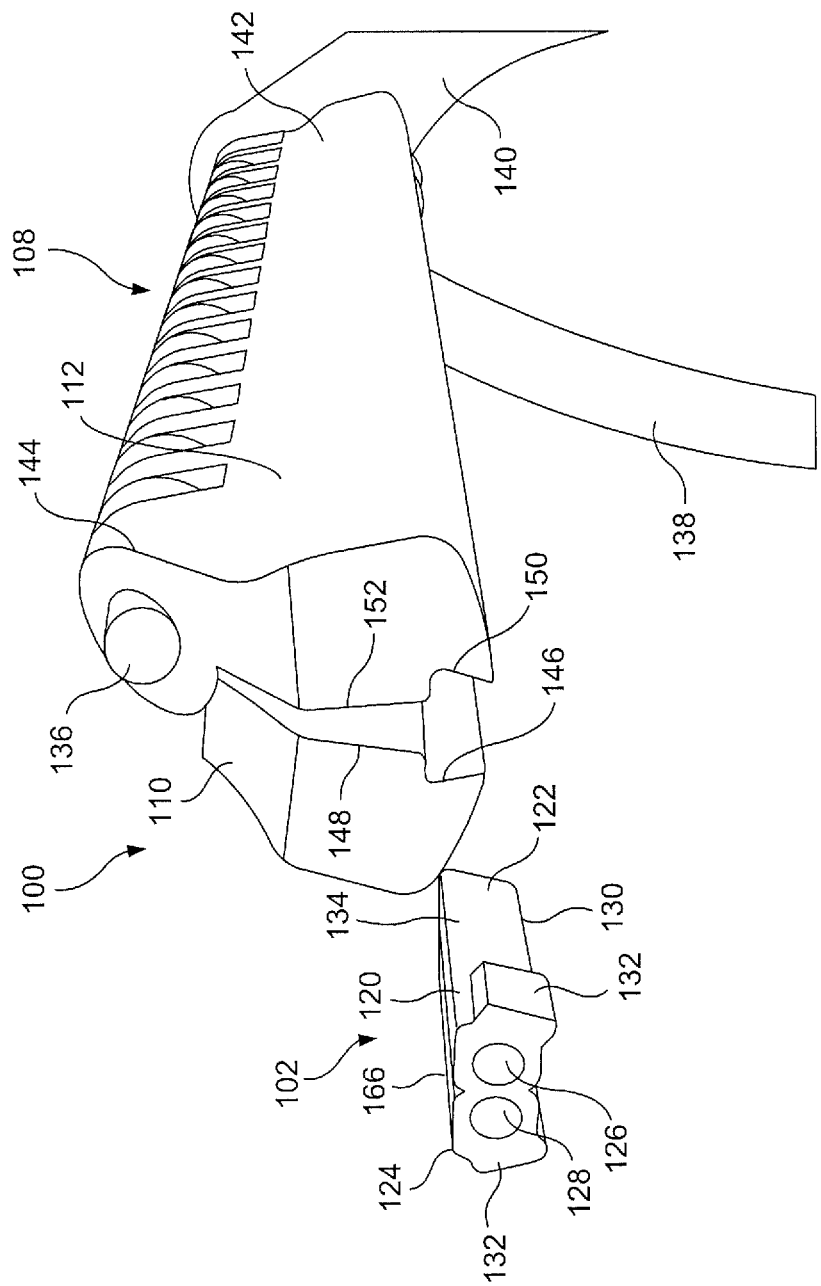
FIG. 1 shows a perspective view of a system according to an exemplary embodiment of the present invention, wherein a crimping tool of the system is in a first configuration.

The present invention may be further understood with reference to the following description and the appended drawings, wherein like elements are referred to with the same reference numerals. The present invention relates to the treatment of bones and, in particular, to methods and devices for fixing bones using bone cerclage techniques. Exemplary embodiments of the present invention describe a system comprising a cable which may be circled around a bone to be fixed and a crimp which may be crimped on the cable using a minimally invasive technique to fix the cable at a desired tension around the bone. It will be understood by those of skill in the art that the terms "proximal" and "distal," as used herein, are intended to refer to a direction toward (proximal) and away from (distal) a user of the device.

Figure 2:
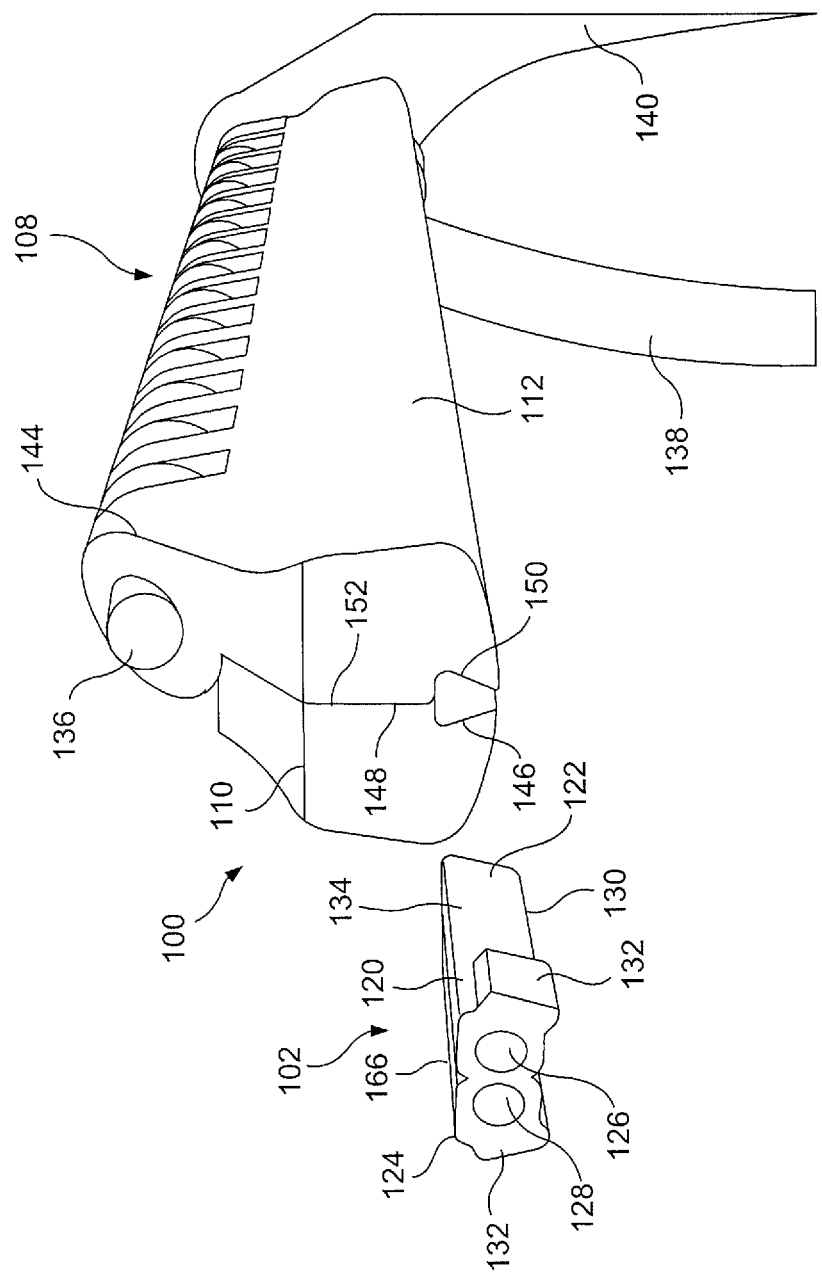
FIG. 2 shows a perspective view of the system of FIG. 1, wherein the crimping tool is in a second configuration.

As shown in FIGS. 1-8, a system 100 according to an exemplary embodiment of the present invention comprises a crimp 102 through which a cable 104 may be passed after it has been looped around a bone 106. The crimp 102 may then be deformed/crushed thereover to fix the cable 104 at a desired tension around the bone 106. The crimp 102 may be deformed using, for example, a crimping tool 108 including first and second portions 110, 112 movable relative to one another between a first crimp-receiving configuration in which the crimp 102 is received therebetween, as shown in FIG. 1, and a second crimping configuration in which the first and second portions 110, 112 are drawn toward one another to deform the crimp 102 held therebetween, as shown in FIG. 2. The first and second portions 110, 112 are sized and shaped to be inserted through a small incision such that the crimp 102 may be deformed during a minimally invasive procedure.

The cable 104 extends from a proximal end 114 to a distal end including a stop 118, which has a larger cross-sectional diameter than a remaining length of the cable 104. As would be understood by those skilled in the art, a length of the cable 104 is preferably selected so that the cable 104 may be looped around the bone 106 and tensioned therearound to fix portions of the bone 106 relative to one another, as desired. The stop 118 may, for example, be ball-shaped and sized to prevent the stop 118 from passing through the crimp 102.

The crimp 102 includes a body 120 extending from a proximal end 122 to a distal end 124 and formed with first and second channels 126, 128, respectively, which extend therethrough from the proximal end 122 to the distal end 124. The body 120 may be sized and shaped to have a low-profile when positioned along the bone 106, including a first surface 130 facing toward the bone 106 and a second surface 166 facing away from the bone 106. The first and second channels 126, 128 are sized and shaped to slidably receive a length of the cable 104 therethrough while preventing the stop 118 from being received therein. In one exemplary embodiment, the first and second channels 126, 128 may be substantially parallel to one another. Thus, the cable 104 may be slid through the first channel 126 such that the stop 118 abuts the distal end 124, looped around the bone 106 and slid through the second channel 128 from the distal end 124 to the proximal end 122 such that a remaining length of cable 104 extends proximally from the proximal end 122.

The body 120 may also include a shoulder 132 extending outward from a lateral surface 134 thereof which extends between the first and second surfaces 130, 132. The shoulder 132 is positioned so as not to interfere with the bone-abutting surface 130 while also acting as a stop permitting only a portion of the body 120 extending proximally from the shoulder 132 to be received within the crimping tool 108. In an exemplary embodiment, the shoulder 132 is positioned at the distal end 124 of the body 120. The crimp 102 according to this embodiment of the invention includes a pair of shoulders 132, extending from opposing sides of the bone-abutting surface 130.

The first and second portions 110, 112 of the crimping tool 108 extend from a proximal end 142 to a distal end 144 of the tool 108 and are connected to one another via a hinge 136 permitting the first and second portions 110, 112 to pivot relative to one another between the first and second configurations. The first and second portions 110, 112 are moved via first and second handles 138, 140 which are connected to the proximal end 142 of the first and second portions 110, 112, respectively. The first and second portions 110, 112 extend laterally from the first and second handles 138, 140 and have a length selected such that the first and second portions 110, 112 may be inserted through a small incision, which may extend along a length of approximately between 10 mm to 50 mm, to a desired depth within a wound to deform/crush the crimp 102.

At the distal end 144, the first portion 110 includes a first recess 146 formed along a surface 148 facing the second portion 112 while the second portion 112 includes a second recess 150 along a surface 152 facing the first portion 110. The first and second recesses 146, 150 face one another and are sized and shaped so that, when the crimping tool 108 is in the first configuration, a recess formed therebetween is sized and shaped to receive a portion of the crimp 102 therebetween. It will be understood by those of skill in the art that the first and second recesses 146, 150 may have any of a variety of shapes and sizes so long as, when combined, the recesses 146, 150 form a cavity sized and shaped to receive the crimp 102 therebetween. In particular, a portion of the crimp 102 proximal of the shoulder 130 may be received therebetween such that the shoulder 132 abuts the distal end 144. In the first configuration, the first and second portions 110, 112 are spaced apart from one another. Once the crimp 102 is received within the first and second recesses 146, 150, the first and second handles 138, 140 are moved toward one another drawing the first and second surfaces 148, 152 of the first and second portions 110, 112 toward one another deforming the crimp 102 over the cable 104.

Figure 3:
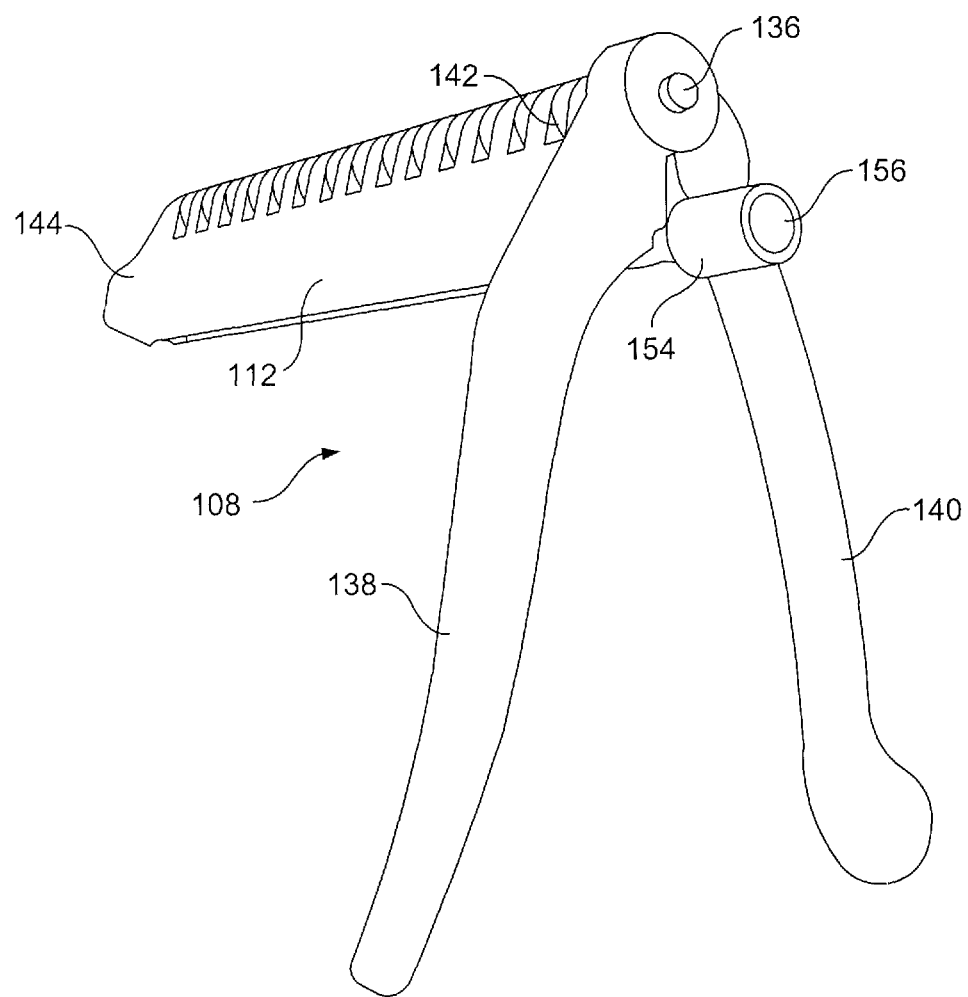
FIG. 3 shows another perspective view of the crimping tool of FIG. 1.

As shown in FIG. 3, the crimping tool 108 may also include a connector 154 extending proximally from the proximal end 142 of the first and second portions 110, 112. The connector 154 includes a lumen 156 extending therethrough and is configured to be connected to a tensioning device to apply tension to a portion of the cable 104 received therein as would be understood by those skilled in the art. Thus, the lumen 156 is sized and shaped to permit the cable 104 to be slidably received therethrough. In an exemplary embodiment, the connector 154 may be substantially tubular.

Figure 4:
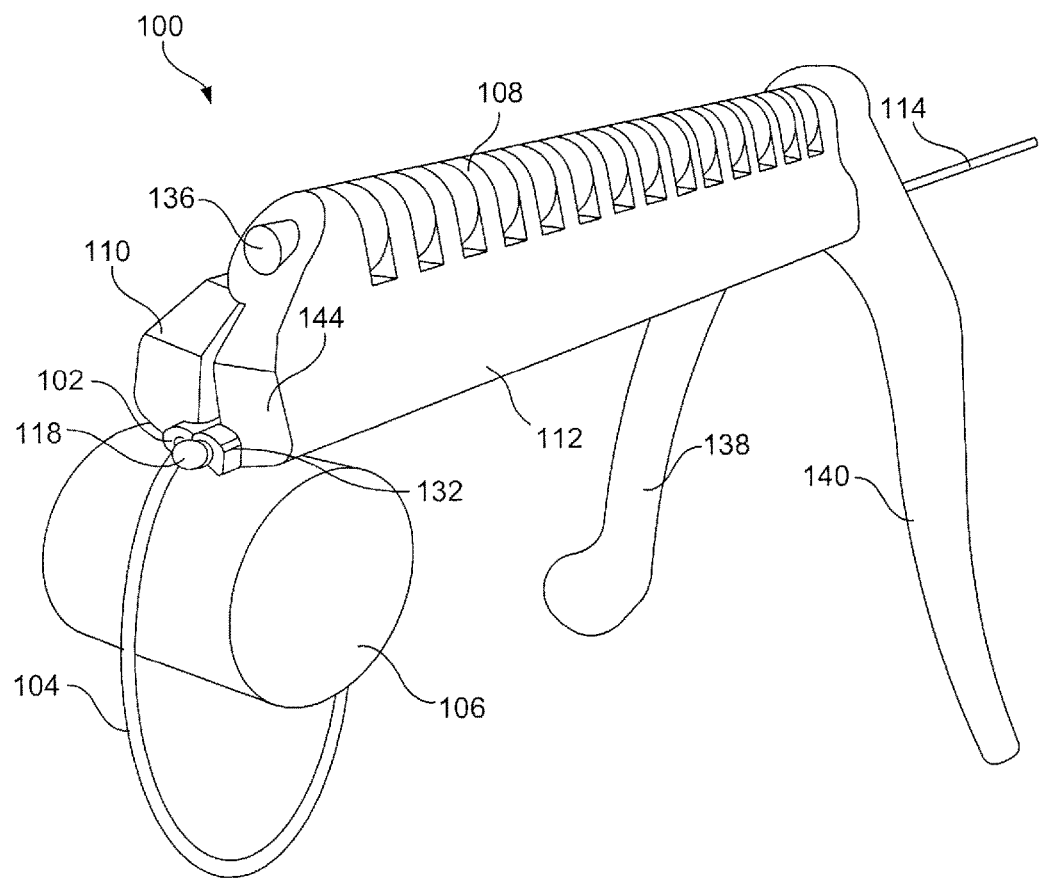
FIG. 4 shows a perspective view of a cable looped around a bone according to the system of FIG. 1.

According to an exemplary surgical technique of the system 100, the cable 104 is inserted through the first channel 126 of the crimp 102 prior to looping the cable 104 about the bone 106. The cable 104 is slid through the first channel 126 until the stop 118 abuts the distal end 124 of the crimp 102. The cable 104 is then looped about the bone 106 using any known cerclage technique and/or tool and the crimp 102 is positioned along the bone 106, as shown in FIG. 4. A remaining length of the lopped cable 104 may then be slid through the second channel 128 from the distal end 124 to the proximal end 122 such that the proximal end 114 of the cable 104 extends proximally from the proximal end 122 of the body 120 and out of an incision through which the crimp 102 and cable 104 have been inserted. The distal end 144 of the first and second portions 110, 112 of the crimping tool 108 are then inserted through the incision to a desired depth within the wound until the distal end 144 reaches the crimp 102.

Figure 5:
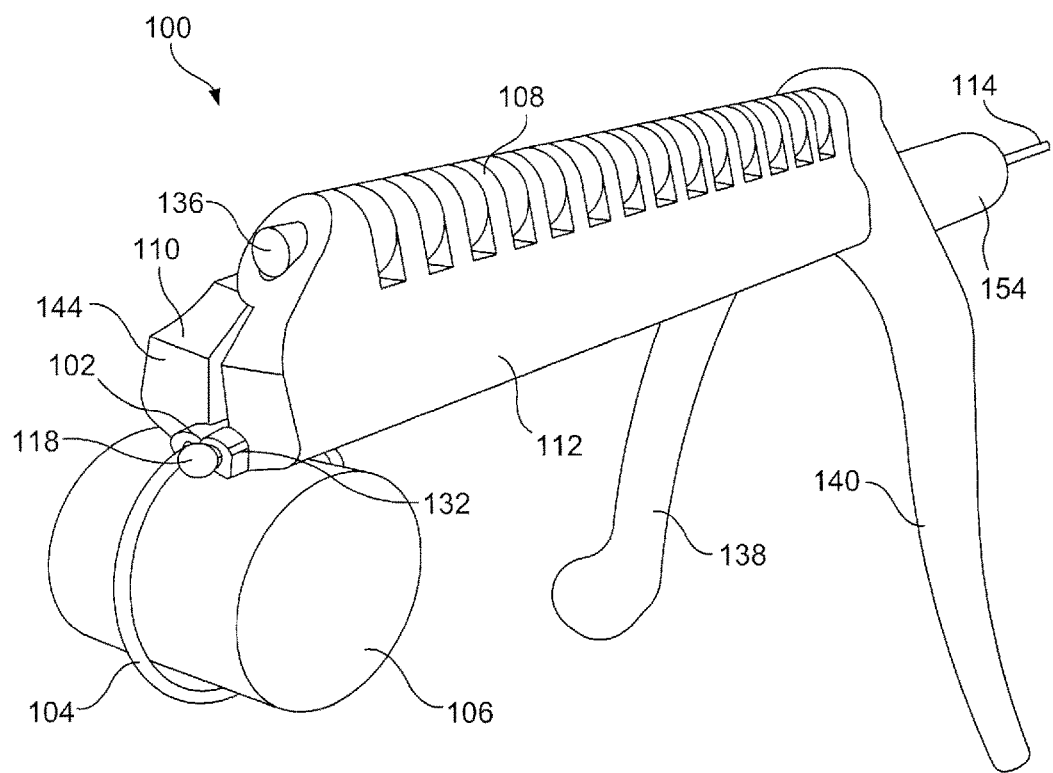
FIG. 5 shows a perspective view of a tension applied to the cable according to the system of FIG. 1.
Figure 6:
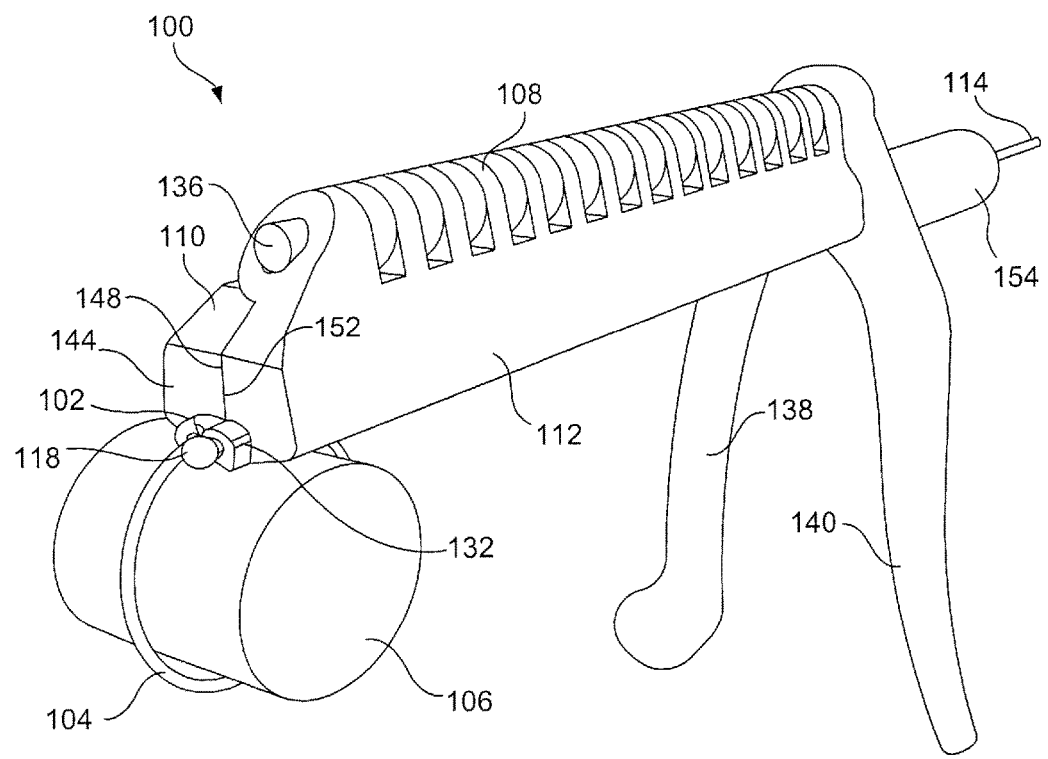
FIG. 6 shows a perspective view of the crimping tool, in the second configuration, to deform a crimp over the tensioned cable according to the system of FIG. 1.
Figure 7:
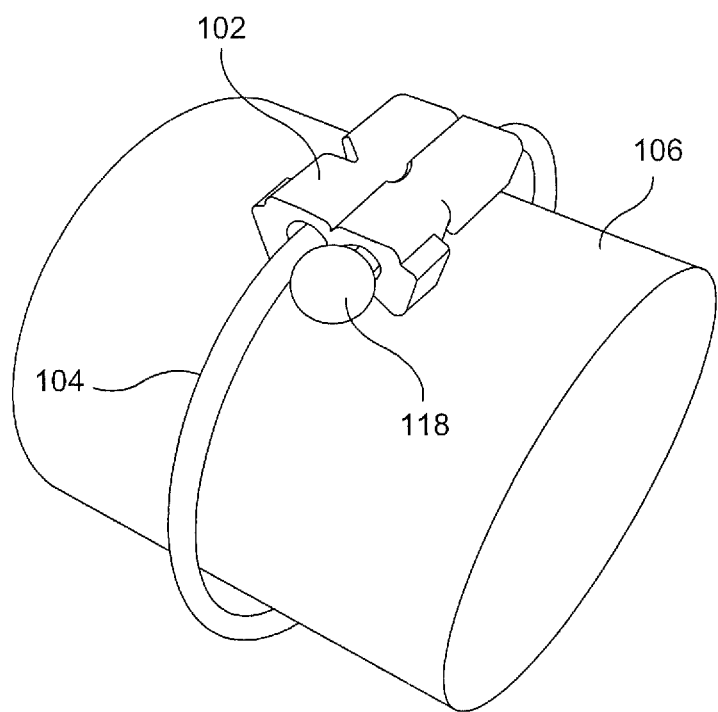
FIG. 7 shows a perspective view of the deformed crimp fixing the cable around the bone at the desired tension according to the system of FIG. 1.

The crimping tool 108 is moved to the first configuration and moved over the crimp 102 such that the body 120 of the crimp 102 is received within the first and second recesses 146, 150 formed by the first and second portions 110, 112 and the shoulder 130 of the crimp 102 abuts the distal end 144. The remaining length of the cable 104 extending proximally from the proximal end 122 of the crimp 102 is passed through the lumen 156 of the connector 154, which is then coupled to a tensioning device to apply a desired tension to the cable 104 encircling the bone 106, as shown in FIG. 5. Once the desired tension has been applied to the cable 104, the crimping tool 108 is moved to the second configuration, as shown in FIG. 6, by moving the handles 138, 140, and thereby the first and second portions 110, 112, toward one another to deform the crimp 102, fixing the crimp 102 over the cable 104 at the desired tension about the bone 106. Once the crimp 102 has been deformed over the cable 104, a length of the cable extending proximally from the proximal end 122 of the crimp 102 may be cut, as shown in FIG. 7, leaving the deformed crimp 102 in place with the cable 104 encircling the bone 106 at the desired tension.

Figure 8:
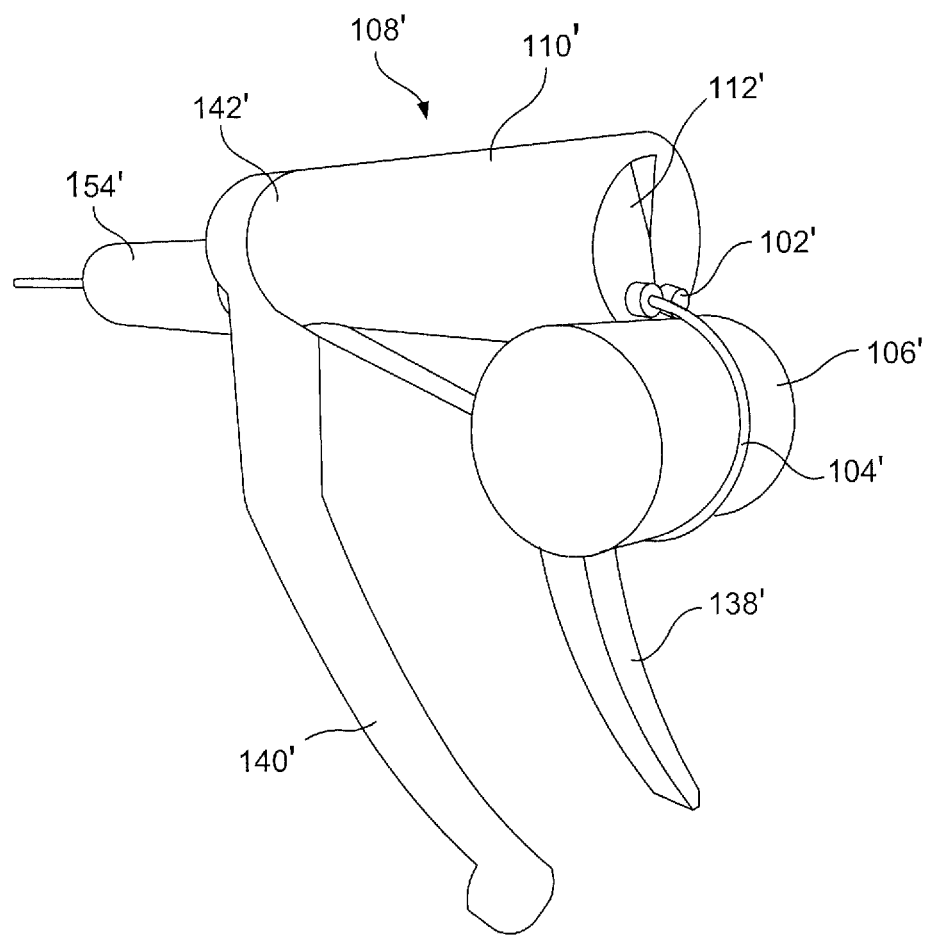
FIG. 8 shows a perspective view of a crimping tool according to an alternate embodiment of the present invention.
Figure 9:
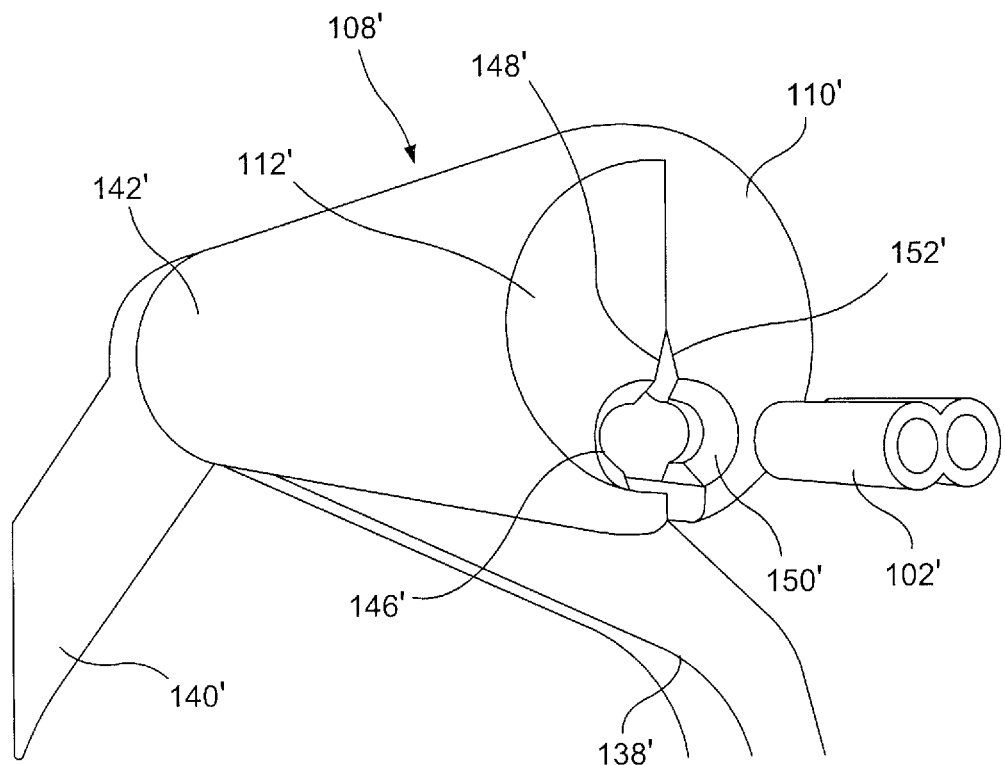
FIG. 9 shows a perspective view of the crimping tool of FIG. 8, in a first configuration.
Figure 10:
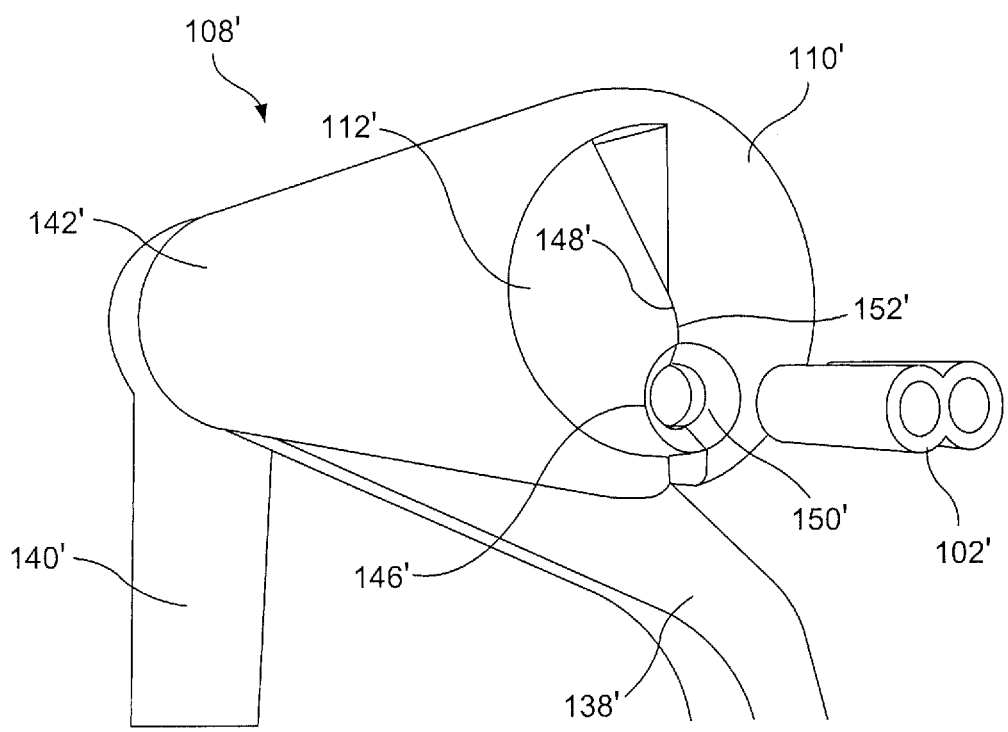
FIG. 10 shows a perspective view of the crimping tool of FIG. 8, in a second configuration.

As shown in FIGS. 8-10, a crimping tool 108' according to an alternate embodiment of the present invention is substantially similar to the crimping tool 108 described above, comprising first and second portions 110', 112', respectively, movable relative to one another between a first crimp receiving configuration and a second crimping configuration. The first and second portions 110', 112', however, do not pivot relative to one another about a hinge. Rather, the first portion 110' is substantially tubular and includes an interior space sized and shaped to receive the second portion 112', which may be partially cylindrical (e.g., hemi-cylindrical) such that the first and second portions 110', 112' may be rotated relative to one another via handles 138', 140' attached to a proximal end 142' thereof. The first and second portions 110', 112' include distal surfaces 148', 150', respectively, including edges which face one another to receive a crimp 102' therebetween. The distal faces 148', 150' form recesses 146', 150', respectively, extending along edges thereof which are sized and shaped to collectively receive the crimp 102' therein. It will be understood by those of skill in the art that the recesses 146', 150' may take any of a variety of shapes and sizes so long as the recesses 146', 150' are sized and shaped to collectively receive the crimp 102'.

In the first configuration, as shown in FIG. 9, the edges of the distal surfaces 148', 150' are spaced from one another to receive the crimp 102' within the recesses 146', 150'. In the second configuration, as shown in FIG. 10, the handles 138', 140' are drawn toward one another such that edges of the distal surfaces 148', 150' are also drawn toward one another to deform/crush the crimp 102' therebetween. Similarly to the crimping tool 108, the crimping tool 108' also includes a connector 154' at the proximal end 142' for connecting to a tensioning device to apply a tension to a cable 106', which has been looped around a bone 106', as described above in regard to the system 100.

Figure 11:
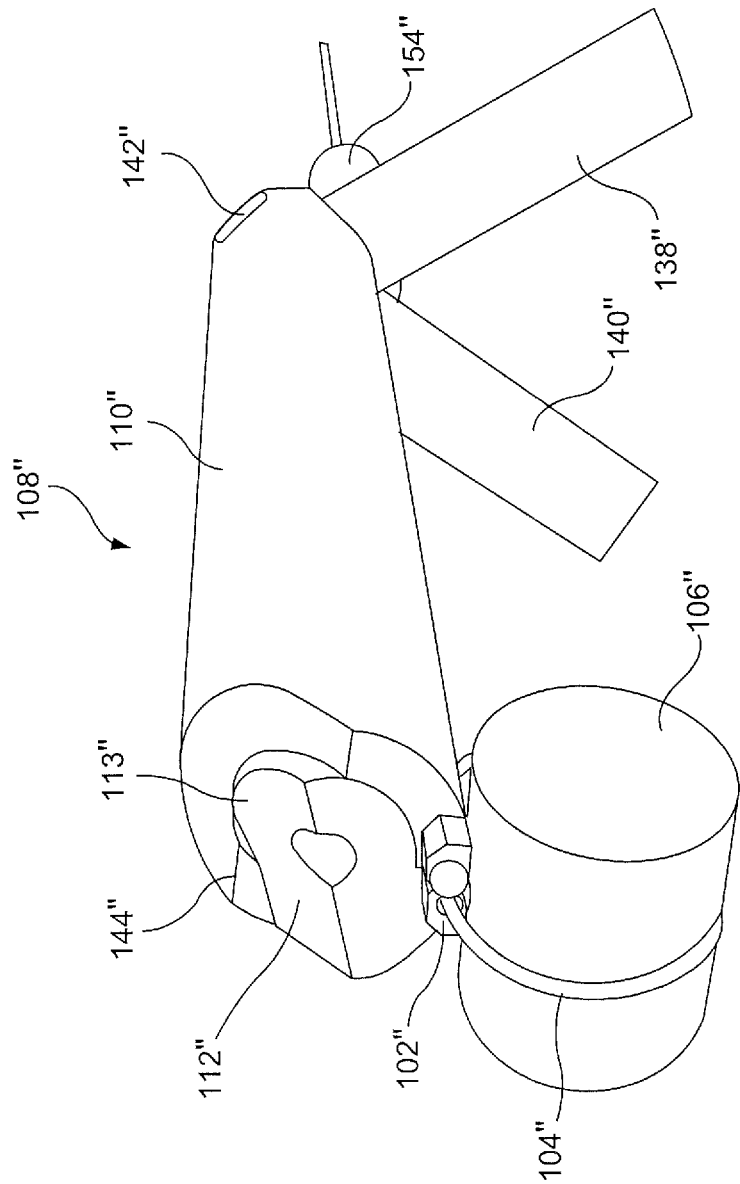
FIG. 11 shows a perspective view of a crimping tool according to another embodiment of the present invention.
Figure 12:
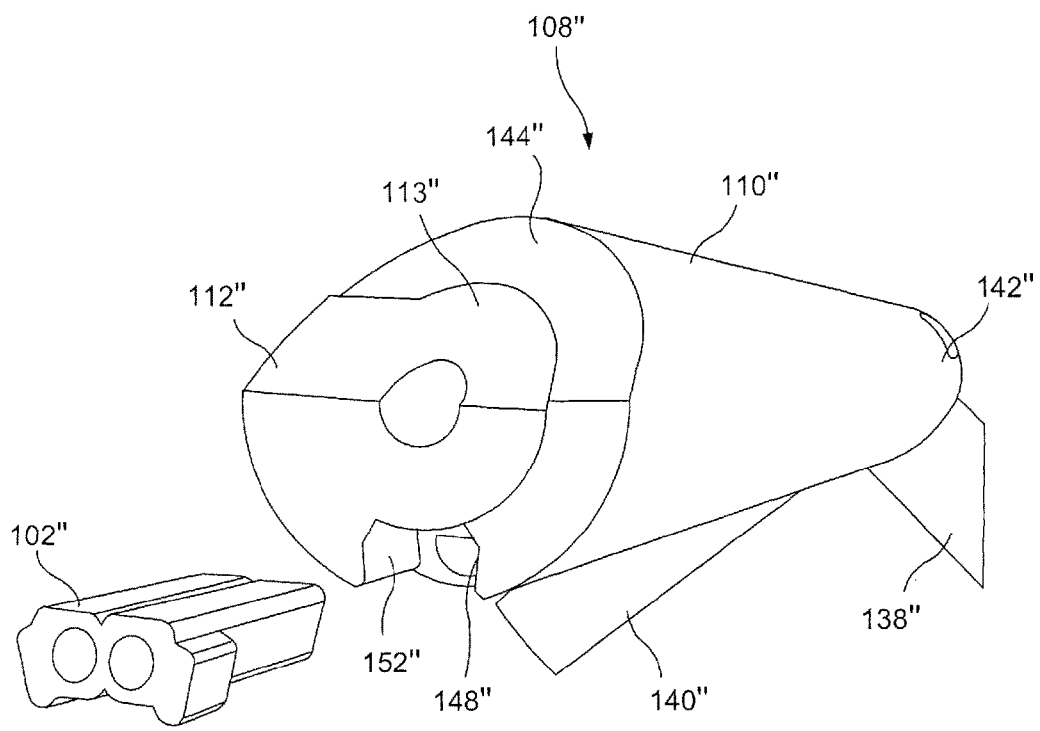
FIG. 12 shows a perspective view of the crimping tool of FIG. 11, in a first configuration.
Figure 13:
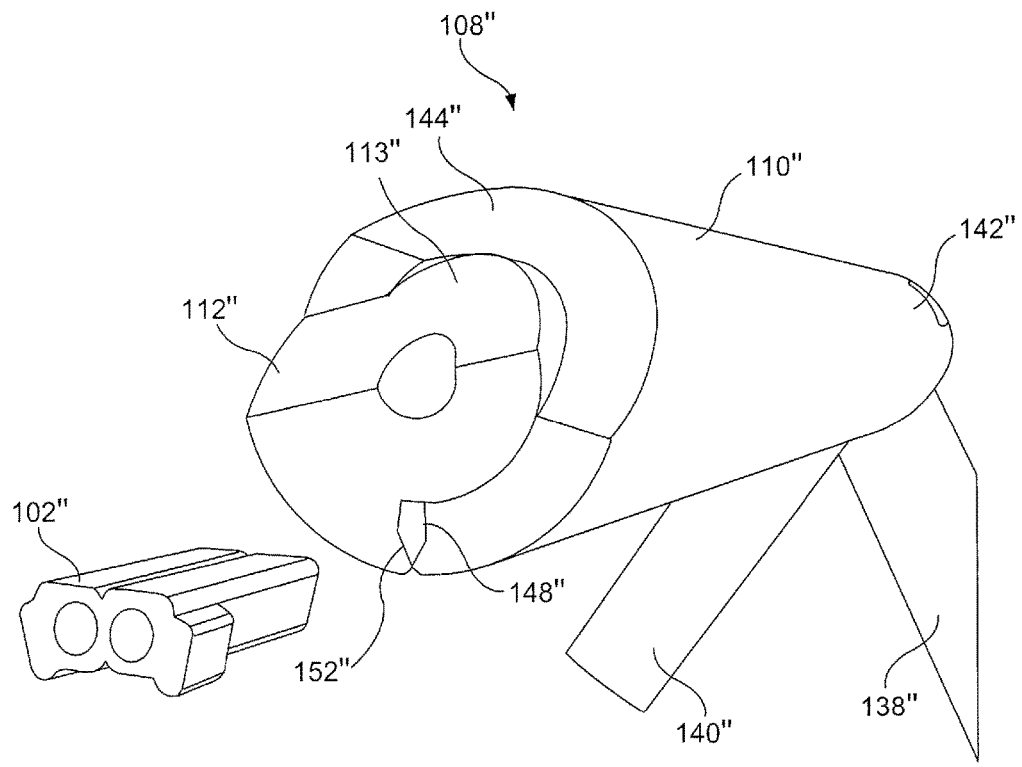
FIG. 13 shows a perspective view of the crimping tool of FIG. 11, in a second configuration.

As shown in FIGS. 11-13, a crimping tool 108" according to another exemplary embodiment of the present invention is substantially similar to the crimping tools 108' described above except as pointed out below. The crimping tool 108" similarly comprises first and second portions 110", 112" movable relative to one another between a first crimp receiving configuration, as shown in FIG. 12, and a second crimping configuration, as shown in FIG. 13, via handles 138", 140" attached to a proximal end 142" thereof. The proximal end 142" also includes a connector 154" for connecting to a device for tensioning a cable 104" passed through a crimp 102" to be crimped via the crimping tool 108". The first portion 110", however, is formed as a partial tube while the second portion 112" is partially received therein such that the first and second portions 110", 112" are rotatable relative to one another about a longitudinal axis of the first portion 110". The partial tube of the first portion 110" extends about an angle greater than 180° such that a rounded portion 113" of the second portion 112" is held therein while also permitting the first and second portions 110", 112" to rotate relative to one another.

At a distal end 144", an edge of the partial tube of the first portion 110" forms a first surface 148" while an edge of the second portion 112" forms a second surface 152" which faces the first surface 148" such that a crimp 102" may be received therebetween, in the first configuration. The first and second surfaces 148", 152" are preferably sized and shaped to correspond to the crimp 102". Thus, when the crimping tool 108" is moved to the second configuration, the first and second surfaces 148", 150" are drawn toward one another to deform/crush the crimp 102" received therebetween, fixing the crimp 102" about a cable 104" which has been looped about a bone 106", as described above in regard to the system 100.

Figure 14:
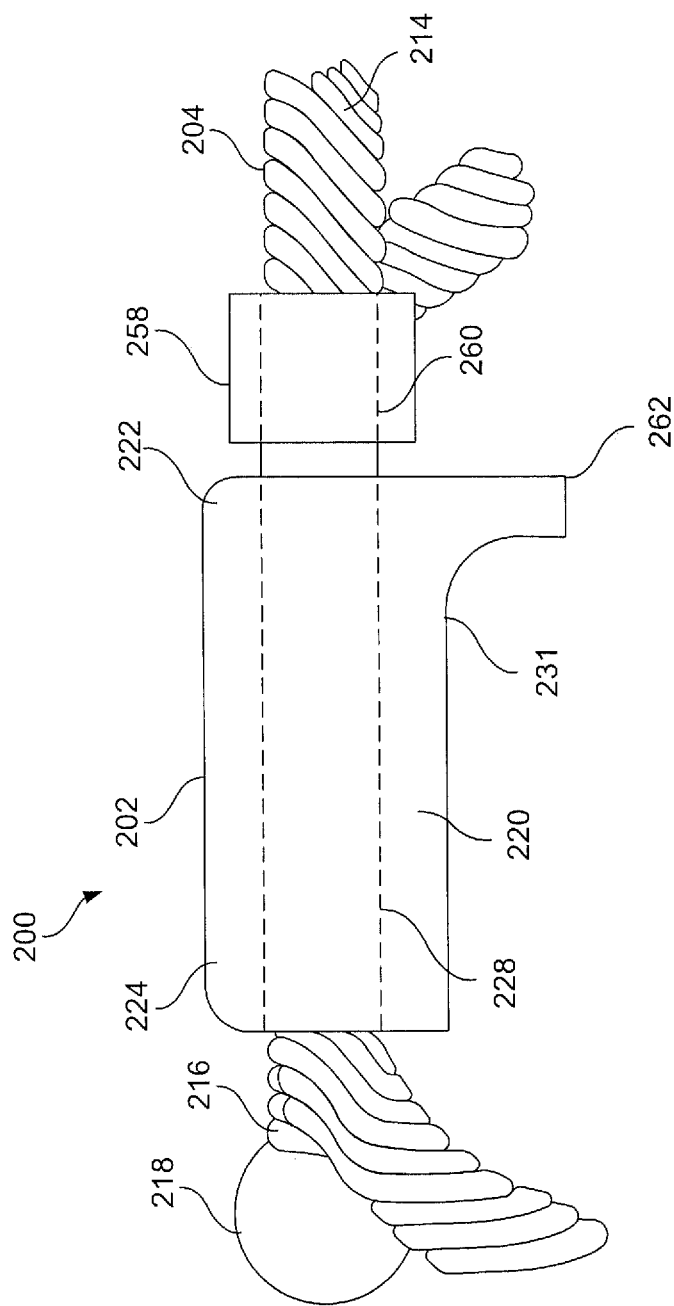
FIG. 14 shows a side view of a system according to another exemplary embodiment of the present invention.
Figure 15:
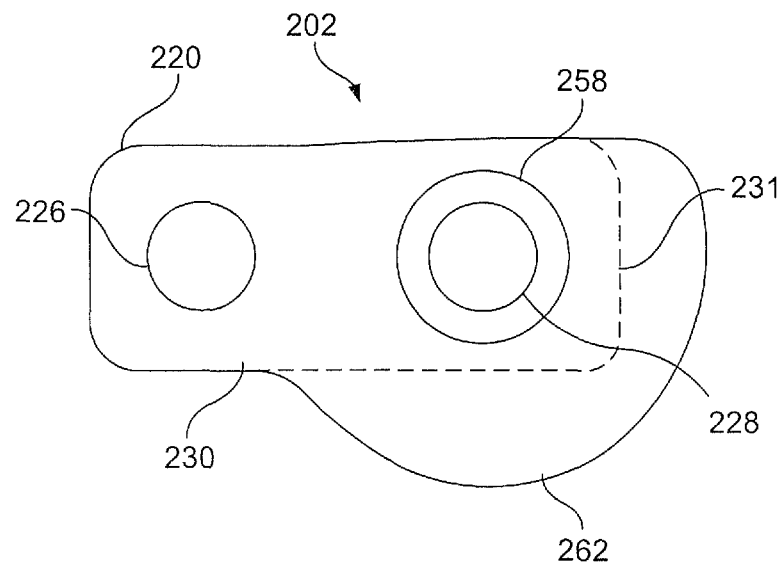
FIG. 15 shows another side view of a crimp of the system of FIG. 14.
Figure 16:
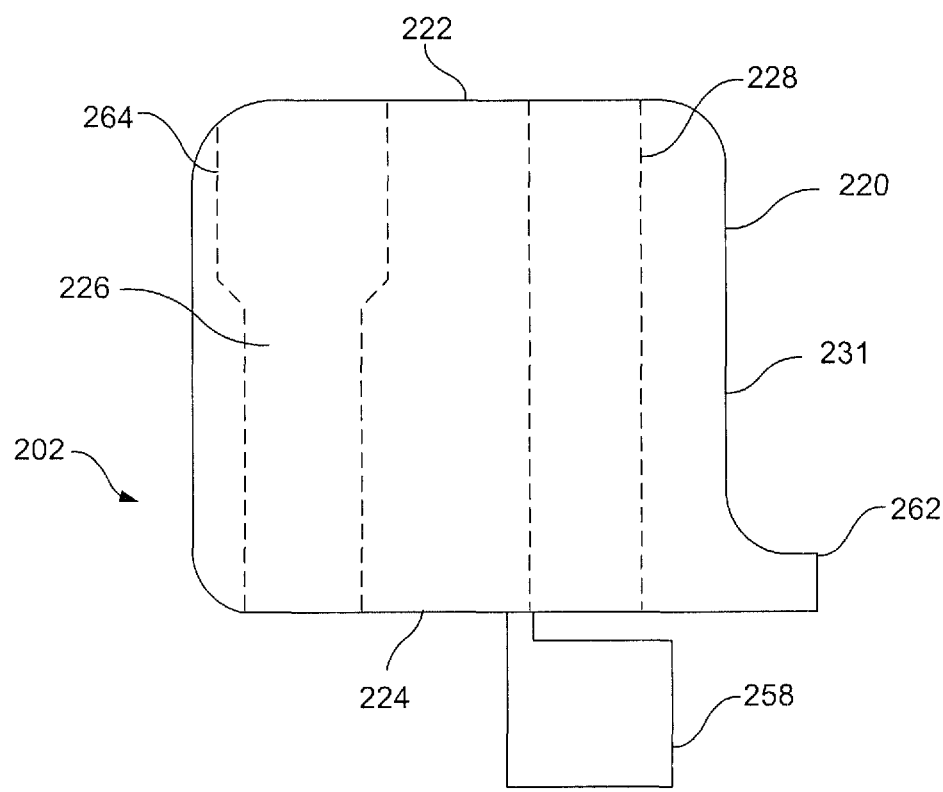
FIG. 16 shows a top plan view of the crimp of FIG. 14.

As shown in FIGS. 14-16, a system 200 according to a second exemplary embodiment of the present invention is substantially similar to the system 100, comprising a crimp 202 and a cable 204 which may be looped around a bone and passed through the crimp 202 such that a portion of the crimp 202 may be deformed and fixed thereover. Although, not shown, the crimp 202 and cable 204 may be utilized with a crimping tool such as, for example, any of the crimping tools 108, 108', 108" described above. It will be understood by those of skill in the art, however, that any crimping tool known in the art may be utilized with the system 200. The cable 204 may be substantially similar to the cable 104, extending from a proximal end 214 to a distal end 216 and including a stop 218 at the distal end 216. The stop 218 may, for example, be ball-shaped. Similarly to the crimp 102, the crimp 202 comprises a body 220 extending from a proximal end 222 to a distal end 224 and including first and second channels 226, 228 extending therethrough from the proximal end 222 to the distal end 224. The first channel 226, however, includes an enlarged portion 264 at a distal end thereof. The enlarged portion 264 is sized and shaped to accommodate the stop 218 of the cable 204 therein such that while a length of the cable 204 is permitted to slide therethrough, the stop 218 is received within the enlarged portion 264 and prevented from passing proximally therepast.

The crimp 202 also further comprises an extension such as, for example, a tube 258 attached to the proximal end 222 of the body 220 such that a lumen 260 of the tube 258 is substantially coaxial with the second channel 228. The lumen 260 is also sized and shaped to permit the length of the cable 204 to be slid therethrough. Once the cable 104 has been looped around the bone, the cable 104 is passed through both the second channel 228 and the tube 258. Rather than deforming/crushing the body 220 of the crimp 202, the tube 258 is crushed over the cable 204 to fix cable 204 about the bone at a desired tension. It will be understood by those of skill in the art that since the tube 258 extends proximally of the proximal end 222 of the body 220, a crimping tool is required to be inserted through an incision to a depth within the wound less than that which would be required to crimp the body 220. Thus, the crimp 202 facilitates a minimally invasive crimping procedure. Although the extension is describes as a tube 258, it will be understood by those of skill in the art that the extension is not required to be tubular in shape, but may be any of a variety of shapes so long as the lumen 260 thereof is sized and shaped to permit the cable 104 to be slid therethrough.

The crimp 202 also comprises a bevel 262 extending laterally from the body 220 at the proximal end 222. The bevel 262 may, for example, extend from a first surface 230 of the body 220 which, when in an operative position, faces the bone and a surface 231 lateral of the bone-facing surface 230 proximate the second channel 228. The bevel 262 is curved, extending about the bone-facing surface 230 and the lateral surface 231 proximate the second channel 228, such that when the crimp 102 is positioned over bone, the bevel 262 comes into contact with the bone. Thus, when the tube 258 is deformed over the cable 204, the tube 258 is tilted toward the bone.

Similarly to the system 100, the cable 204 may be pre-assembled with the crimp 202 by inserting the cable 204 through the first channel 226 until the stop 218 is received within the enlarged portion 264. The assembled crimp 202 and cable 204 may then be positioned over the bone and the cable 204 looped/circled around the bone. A length of the looped cable 204 is then inserted through the second channel 228 and the tube 258 from the distal end 224 to the proximal end 222 such that a remaining length of the cable 204 extends proximally out of the incision. The crimping tool 108, or any other known crimping tool, may be inserted into the wound and until the tube 258 is received between first and second portions 110, 112 thereof. A tension may be applied to the cable 204 until the cable 204 is at a desired tension about the bone. The first and second portions 110, 112 of the crimping tool 108 may then be brought together to crush and thereby deform the tube 258 over the cable 204 at the desired tension.

Figure 17:
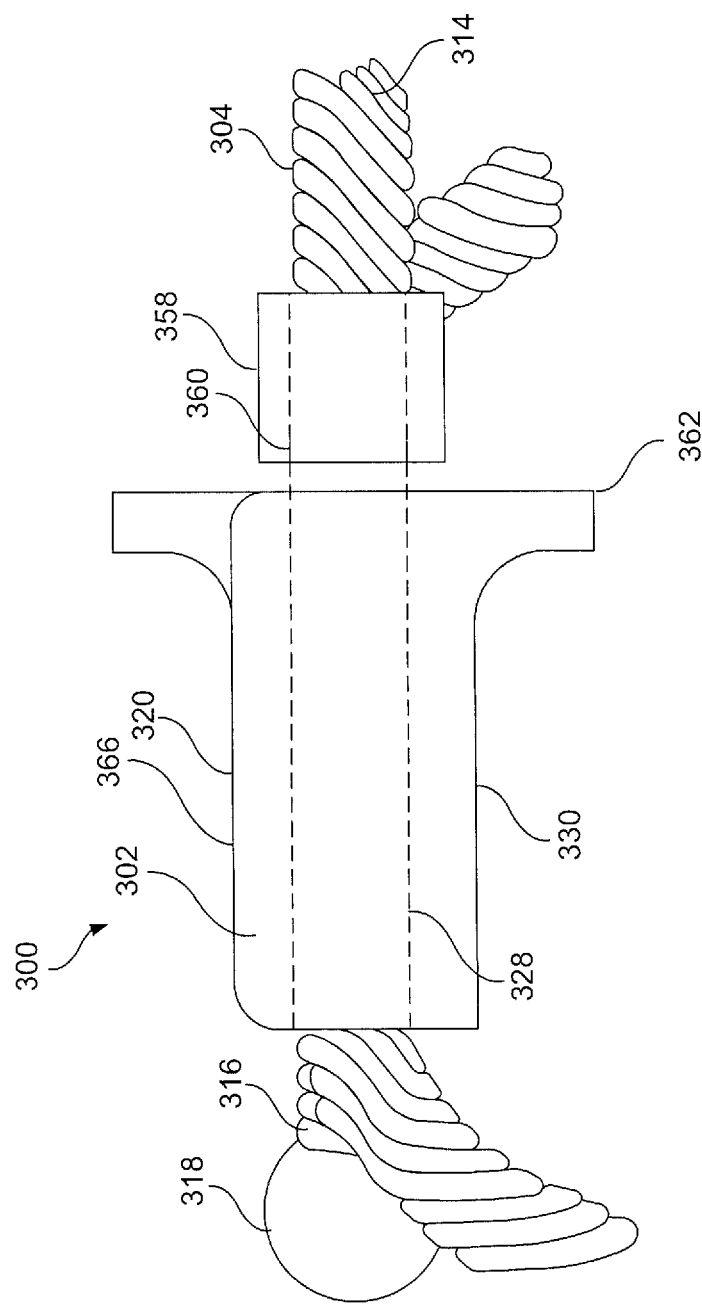
FIG. 17 shows a side view of a system according to yet another exemplary embodiment of the present invention.

As shown in FIGS. 17-19, a system 300 may be substantially similar to the system 200, described above, comprising a crimp 302 and cable 304 which may be looped around a bone and passed through the crimp 302. The cable 304 may be substantially similar to the cables 104, 204 described above in regard to the systems 100, 200, extending from a proximal end 314 to a distal end 316 and including a stop 318 at the distal end 316. The crimp 302 may be substantially similar to the crimp 202, comprising a body 320 extending from a proximal end 322 to a distal end 324 and including first and second channels 326, 328 extending therethrough. The first channel 326 includes an enlarged portion 364 sized and shaped to accommodate the stop 318 therein. Similarly to the crimp 202, the crimp 302 also includes a tube 358 attached to the proximal end 322 of the body 320 such that a lumen 360 thereof is coaxial with the second channel 328 and a bevel 362 extending laterally from the proximal end 322. The crimp 302, however, is substantially symmetrical about an axis A such that the bevel 362 extends laterally outward from a first surface 330, a second surface 366 opposing the first surface 330 and a lateral surface 331 extending therebetween. The bevel 362 extends outward from a portion of the body 320 extending about the second channel 328 such that the bevel 362 appears to extend substantially radially outward from the second channel 328.

The extension of the bevel 362 about the body 320 permits either of the first or second surfaces 330, 366 to be utilized as the bone-abutting surface such that the crimp 302 is not required to be positioned over the bone in a particular orientation in which one of the first and second surfaces 330, 362 faces toward the bone. It will be understood by those of skill in the art that the system 300 may be utilized in a manner substantially similarly to the system 200, described above. When either the first or second surfaces 330, 366 of the crimp 302 contact the bone, the bevel 362 facilitates tilting of the tube 358 toward the bone as the tube 358 is deformed/crushed over the cable 304 using a crimping tool. It will be understood by those of skill in the art that the tube 358 may be crimped using any of the crimping tools 108, 108', 108", described above, or any other known crimping tool.

It will be apparent to those skilled in the art that various modifications and variations can be made in the structure and methodology of the present invention, without departing from the spirit or scope of the invention. Thus, it is intended that the present invention cover the modifications and variations of this invention provided that they come within the scope of the appended claims and their equivalents.

What is claimed is:

1. A crimp configured to fix a cable about a bone, comprising:
    a body extending from a proximal end to a distal end;
    a first channel extending through the body from the proximal end to the distal end, the first channel being sized and shaped to permit a cable to be slid therethrough;
    a second channel extending through the body from the proximal end to the distal end, the second channel being sized and shaped to permit a cable to be slid therethrough; and
    a deformable extension attached to the proximal end of the body, the extension including a lumen aligned with the second channel and sized and shaped to permit the cable to be slid therethrough.

2. The crimp according to claim 1, further comprising a bevel extending laterally outward from a bone-abutting surface proximate the second channel at the proximal end of the body.

3. The crimp according to claim 2, wherein the bevel extends substantially radially outward from the a portion of the body surrounding the second channel.

4. The crimp according to claim 2, wherein the bevel includes a curved surface for contacting the bone.

5. The crimp according to claim 1, wherein the first channel includes an enlarged portion at the proximal end of the body, the enlarged portion sized and shaped to receive a stop at a distal end of a cable.

6. The crimp according to claim 1, wherein the first and second channels are substantially parallel to one another.

7. The crimp according to claim 1, wherein the extension is substantially tubular.

8. A system for fixing a cable about a bone, comprising:
    a cable extending from a proximal end to a distal end and including a stop at the distal end thereof;
    a crimp including a body extending from a proximal end to a distal end, the body including:
        a first channel extending therethrough from the proximal end to the distal end and being sized and shaped to permit a length of the cable to be slid therethrough while preventing the stop from passing therethrough;
        a second channel extending therethrough from the proximal end to the distal end and being sized and shaped to permit the cable to be slid therethrough; and
        an extension attached to the proximal end of the body, the extension including a lumen aligned with the second channel and sized and shaped to permit the cable to be slid therethrough; and
    a crimping tool including a first and second portion movable relative to one another between a first configuration in which the extension of the crimp is received between the first and second portions and a second configuration in which the first and second portions are drawn together to crush the extension over the cable.

9. The system according to claim 8, wherein the first and second portions of the crimping tool are connected via a hinge such that the first and second portions are pivotable relative to one another.

10. The system according to claim 8, wherein the first portion is substantially tubular and the second portion is partially cylindrical and received within the first portion such that the first and second portions are rotatable relative to one another about a longitudinal axis thereof.

11. The system according to claim 8, wherein the first portion is partially tubular to receive a rounded portion of the second portion such that the first and second portions are rotatable relative to one another about a longitudinal axis thereof.

12. The system according to claim 8, further comprising a first handle attached to a proximal end of the first portion and a second handle attached to a proximal end of the second portion for moving the first and second portions between the first and second configuration.

13. The system according to claim 8, wherein the first channel includes an enlarged portion sized and shaped to receive the stop of the cable therein.

14. The system according to claim 8, wherein the first and second portions include first and second recesses, respectively, at distal ends thereof which are sized and shaped to correspond to a size and shape of the crimp.

15. The system according to claim 8, wherein the crimp includes a connector configured for connection to a tensioning device for applying tension to the cable.

* * * * *

UNITED STATES PATENT AND TRADEMARK OFFICE
CERTIFICATE OF CORRECTION

PATENT NO. : 9,642,660 B2
APPLICATION NO. : 13/310244
DATED : May 9, 2017
INVENTOR(S) : Dell'Oca Page 1 of 1

It is certified that error appears in the above-identified patent and that said Letters Patent is hereby corrected as shown below:

In the Claims

Claim 3, Column 7, Line 66:
"extends substantially radially outward from the a portion of" should read "extends substantially radially outward from a portion of".

Signed and Sealed this
Twenty-second Day of May, 2018

Andrei Iancu
*Director of the United States Patent and Trademark Office*